US009488630B2

(12) United States Patent
Coram et al.

(10) Patent No.: US 9,488,630 B2
(45) Date of Patent: Nov. 8, 2016

(54) INTEGRATED REMOTE AERIAL SENSING SYSTEM

(71) Applicant: DOW AGROSCIENCES LLC, Indianapolis, IN (US)

(72) Inventors: Tristan Coram, Zionsville, IN (US); Yang Yang, Zionsville, IN (US); Terry R. Wright, Carmel, IN (US); Pradeep Setlur, Carmel, IN (US); Fikru Haile, Carmel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 145 days.

(21) Appl. No.: 14/535,118

(22) Filed: Nov. 6, 2014

(65) Prior Publication Data

US 2015/0134152 A1    May 14, 2015

Related U.S. Application Data

(60) Provisional application No. 61/901,940, filed on Nov. 8, 2013.

(51) Int. Cl.
*B64B 1/50* (2006.01)
*B64B 1/44* (2006.01)
(Continued)

(52) U.S. Cl.
CPC ............. *G01N 33/0098* (2013.01); *B64B 1/44* (2013.01); *B64B 1/50* (2013.01); *B64B 1/66* (2013.01);
(Continued)

(58) Field of Classification Search
CPC ............. B64B 1/44; B64B 1/50; B64B 1/66; B64F 1/12; B64F 1/14; B64D 47/08; B64C 39/022; B64C 2201/148; F03D 5/00; G01N 33/0098

USPC ................................................. 701/3; 244/33
See application file for complete search history.

(56) References Cited

U.S. PATENT DOCUMENTS 3,045,952 A * 7/1962 Underwood ......... H01Q 1/1292
244/33
3,748,471 A    7/1973 Roberts et al.
(Continued)

FOREIGN PATENT DOCUMENTS

AU          771365      12/2000
CA         2436203       8/2002
(Continued)

OTHER PUBLICATIONS

Krout et al. "Tracking Drifting Surface Objects with Aerial Infrared and Electro-Optical Sensors", Oceans, 2012, pp. 1-4.
(Continued)

*Primary Examiner* — Khoi Tran
*Assistant Examiner* — Robert Nguyen
(74) *Attorney, Agent, or Firm* — Eric J. Kraus; Faegre Baker Daniels LLP

(57) ABSTRACT

A system for high temporal and high spatial resolution monitoring of a field of plants is disclosed. Illustratively, the system includes a plurality of ground based reference objects, a balloon adapted to be positioned above the field of plants, and a balloon positioning system coupled to the balloon and configured to position the balloon relative to the field of plants. An imaging system is supported by the balloon and includes a locations system, at least one camera, and at least one gimbal configured to orient the at least one camera. The imaging system captures at least one image of the field of plants including the plurality of ground based reference objects in the at least one image.

27 Claims, 7 Drawing Sheets

(51) Int. Cl.

| | | |
|---|---|---|
| B64D 47/08 | (2006.01) | |
| G05D 1/00 | (2006.01) | |
| G01N 33/00 | (2006.01) | |
| B64F 1/14 | (2006.01) | |
| B64C 39/02 | (2006.01) | |
| B64B 1/66 | (2006.01) | |
| B64F 1/12 | (2006.01) | |
| F03D 5/00 | (2006.01) | |
| G05D 1/08 | (2006.01) | |

(52) U.S. Cl.
CPC ............ *B64C 39/022* (2013.01); *B64D 47/08* (2013.01); *B64F 1/12* (2013.01); *B64F 1/14* (2013.01); *F03D 5/00* (2013.01); *G05D 1/00* (2013.01); *G05D 1/0094* (2013.01); *G05D 1/0866* (2013.01); *B64C 2201/148* (2013.01)

(56) References Cited

U.S. PATENT DOCUMENTS

| | | | |
|---|---|---|---|
| 5,055,679 A | 10/1991 | Ninomiya et al. | |
| 5,353,953 A | 10/1994 | Sakaemura | |
| 5,389,781 A | 2/1995 | Beck et al. | |
| 5,412,219 A | 5/1995 | Chappelle et al. | |
| 5,467,271 A | 11/1995 | Abel et al. | |
| 5,677,532 A | 10/1997 | Duncan et al. | |
| 5,764,819 A | 6/1998 | Orr et al. | |
| 5,784,162 A | 7/1998 | Cabib et al. | |
| 5,859,700 A | 1/1999 | Yang | |
| 6,160,617 A | 12/2000 | Yang | |
| 6,160,902 A | 12/2000 | Dickson et al. | |
| 6,195,039 B1 * | 2/2001 | Glass, Jr. ............ | B63C 9/0005 342/357.75 |
| 6,212,824 B1 | 4/2001 | Orr et al. | |
| 6,366,681 B1 | 4/2002 | Hutchins | |
| 6,442,293 B1 | 8/2002 | Ito et al. | |
| 6,466,321 B1 | 10/2002 | Satake et al. | |
| 6,505,146 B1 | 1/2003 | Blackmer | |
| 6,567,537 B1 | 5/2003 | Anderson | |
| 6,596,996 B1 | 7/2003 | Stone et al. | |
| 6,608,559 B1 | 8/2003 | Lemelson et al. | |
| 6,662,185 B1 | 12/2003 | Stark et al. | |
| 6,683,970 B1 | 1/2004 | Satake et al. | |
| 6,822,742 B1 | 11/2004 | Kalayeh et al. | |
| 6,889,620 B2 | 5/2005 | Fraisse et al. | |
| 7,058,197 B1 | 6/2006 | McGuire et al. | |
| 7,068,816 B1 | 6/2006 | Knoblauch et al. | |
| 7,123,750 B2 | 10/2006 | Lu et al. | |
| 7,411,196 B2 | 8/2008 | Kalaych | |
| 8,085,308 B2 | 12/2011 | Icho et al. | |
| 8,505,847 B2 * | 8/2013 | Ciampa ............ | B64B 1/62 244/24 |
| 8,587,664 B2 * | 11/2013 | McKeown ............ | G01C 11/02 340/577 |
| 8,678,309 B2 * | 3/2014 | Heppe ............ | B64B 1/00 244/29 |
| 9,102,405 B2 * | 8/2015 | Zhang ............ | B64C 39/022 |
| 9,151,272 B2 * | 10/2015 | Goessling ............ | F03D 9/002 |
| 2002/0098593 A1 | 7/2002 | Nelson et al. | |
| 2003/0018431 A1 | 1/2003 | Hanson | |
| 2003/0019151 A1 | 1/2003 | Raun et al. | |
| 2003/0152292 A1 | 8/2003 | Scott et al. | |
| 2004/0034450 A1 | 2/2004 | Seal et al. | |
| 2004/0130713 A1 | 7/2004 | O'Mongain | |
| 2004/0231239 A1 | 11/2004 | Raun et al. | |
| 2005/0038568 A1 | 2/2005 | Hood et al. | |
| 2005/0089219 A1 | 4/2005 | Zhang | |
| 2005/0149235 A1 | 7/2005 | Seal et al. | |
| 2006/0006335 A1 | 1/2006 | Lawrence et al. | |
| 2006/0074560 A1 | 4/2006 | Dyer et al. | |
| 2006/0229814 A1 | 10/2006 | Faivre et al. | |
| 2006/0268947 A1 | 11/2006 | Kalayeh | |
| 2007/0186313 A1 | 8/2007 | Lightner et al. | |
| 2007/0208512 A1 | 9/2007 | Glenn et al. | |
| 2007/0217689 A1 | 9/2007 | Yang et al. | |
| 2009/0046890 A1 | 2/2009 | Hausmann et al. | |
| 2011/0261165 A1 | 10/2011 | Kochi et al. | |
| 2012/0105634 A1 | 5/2012 | Meidan et al. | |
| 2012/0314068 A1 | 12/2012 | Schultz | |
| 2013/0027554 A1 * | 1/2013 | Meadow ............ | 348/144 |
| 2013/0195362 A1 * | 8/2013 | Janky ............ | G01C 15/00 382/195 |
| 2014/0312165 A1 * | 10/2014 | Mkrtchyan ............ | B64D 47/08 244/13 |
| 2015/0022656 A1 * | 1/2015 | Carr ............ | G06K 9/0063 348/117 |
| 2015/0158587 A1 * | 6/2015 | Patrick ............ | B64C 39/024 244/137.4 |
| 2016/0050840 A1 * | 2/2016 | Sauder ............ | A01B 76/00 701/3 |

FOREIGN PATENT DOCUMENTS

| | | |
|---|---|---|
| CA | 2454827 | 2/2003 |
| CN | 1715873 | 1/2006 |
| CN | 1793857 | 6/2006 |
| CN | 1837787 | 9/2006 |
| CN | 1895025 | 1/2007 |
| CN | 1975378 | 6/2007 |
| CN | 101021472 | 8/2007 |
| CN | 101074925 | 11/2007 |
| CN | 101210876 | 7/2008 |
| EP | 1791090 | 5/2007 |
| JP | 2002360070 | 12/2002 |
| JP | 2004003878 | 1/2004 |
| JP | 2004151278 | 5/2004 |
| JP | 2005308733 | 11/2005 |
| JP | 2007143490 | 6/2007 |
| JP | 2007310463 | 11/2007 |
| RU | 2308679 | 10/2007 |
| RU | 2337518 | 11/2008 |
| WO | 9919824 | 4/1999 |
| WO | 02069230 | 9/2002 |
| WO | 2006113582 | 10/2006 |
| WO | 2007146176 | 12/2007 |

OTHER PUBLICATIONS

Banno et al. "Shape Recovery of 3D Data Obtained from a Moving Range Sensor by using Image Sequences", Tenth IEEE International Conference on Computer Vision, 2005, 1, pp. 792-799.

Miyamoto et al. "Classification of Wetland Vegetation Using Aerial Photographs by Captive Balloon Cameras and Aero NIR Color Video Image, Kushiro Northern Wetland in Japan", IEEE 2001 International Geoscience and Remote Sensing Symposium, 2001, 4, pp. 1982-1984.

Walberg, et al. "Effects of Nitrogen Nutrition on the Growth, Yield, and Reflectance Characteristics of Corn Canopies," Agronomy Journal, vol. 74, No. 4, pp. 677-83 (1981).

Blackmer et al. "Transmittance and Reflectance Measurements of Corn Leaves from Plats with Different Nitrogen and Water Supply," J. Plant Physical, vol. 148, pp. 523-29 (1996).

Filella et al. "Relationship Between Photosynthetic Radiation-Use Efficiency of Barley Canopies and the Photochemical Reflectance Index," Physiologia Plantarum, vol. 96, pp. 211-216 (1996).

Osborne et al. "Detection of Phosphorus and Nitrogen Deficiencies in Corn Using Spectral Radiance Measurements," Agronomy Journal, vol. 94, No. 6, pp. 1215-1221 (2002).

Fundamentals of Remote Sensing, Canada Center for Remote Sensing, viewed Jan. 17, 2016, https://www.nrcan.gc.ca/sites/www.nrcan.gc.ca/.../fundamentals_e.pdf.

Dr. Nicholas Short, The Remote Sensing Tutorial, viewed Jan. 17, 2016, updated Jan. 2006, http://fas.org/irp/imint/docs/rst/Front/overview.html.

The Infrared Prcoessing and Analysis Center (IPAC), Infrared Windows, viewed Jan. 17, 2016, http://www.ipac.caltech.edu/.

(56) References Cited

OTHER PUBLICATIONS

National University of Singapore, Optical Remote Sensing, viewed Jan. 17, 2016, updated Aug. 2004, http://www.crisp.nus.edu.sg/~research/tutorial/optical.htm.

Paul J. Pinter, Jr. et al., Remote Sensing for Crop Management, Journal of Photogrammetric Engineering & Remote Sensing, Jun. 2003, vol. 69, No. 6, pp. 647-664.

Michele R. Slaton et al., Estimating Near-Infrared Leaf Reflectance from Leaf Structural Characteristics, American Journal of Botany, Feb. 2001, vol. 88, No. 2, pp. 278-284.

Qui-Xiang Yi et al., Monitoring Rice Nitrogen Status Using Hyperspectral Reflectance and Artificial Neural Network, Environ. Sci. Technol., Sep. 2007, vol. 41, No. 19, pp. 6770-6775.

Sina Keshavarzi & Darin Lickfeldt, Remoting Sensing: Identification of University Research & Evalyation of Relevant IPRs, dated May 2009, 79 pages.

\* cited by examiner

INTEGRATED REMOTE AERIAL SENSING SYSTEM

CROSS-REFERENCE TO RELATED APPLICATIONS

This application claims priority to U.S. Provisional Patent Application Ser. No. 61/901,940, filed on Nov. 8, 2013, the disclosure of which is expressly incorporated by reference herein. This application is also related to U.S. Provisional Patent Application Ser. No. 61/901,957, filed on Nov. 8, 2013, the disclosure of which is expressly incorporated by reference herein.

BACKGROUND AND SUMMARY

The present invention relates generally to aerial sensing systems and, more particularly, to an aerial platform with sensors to achieve high spatial, temporal and spectral resolution of a field of plants.

Traditional aerial platforms such as boom lifts, fixed-wing aircrafts and/or satellites present challenges in the application of remote sensing to plant performance monitoring. Conventional ladder or boom lifts are typically positioned too low above the field of plants (e.g., less than 50 feet altitude) to provide sufficient plant coverage and data collection. In contrast, satellites and aircraft are typically positioned too high above the field of plants (e.g., greater than 500 feet altitude). Moreover, images acquired by satellites are normally low in resolution both spatially and temporally. Aircraft based remote sensing systems generally cannot fly below certain altitudes and are not configured to provide images at the spatial resolutions typically required in phenotype screening of plants.

A helium balloon may fill the gap in altitudes between 50 feet to 500 feet (where ladder or boom-lifts are too low and manned aircraft are too high). Such balloon based image systems are known for use in crop monitoring systems. However, conventional balloon systems are normally effective only in relatively light wind conditions, and are difficult to position and hold steady. Moreover, accurately establishing a precise camera location or acquiring aerial images along an outline track remains challenging, if not impossible with conventional balloon-based imaging systems.

High-temporal frequency crop sensing demands a system that is able to collect large amounts of images of targeted fields. High-spatial resolution means that minor differences between targets of interest and their surroundings, such as soil backgrounds, are well established in each acquired image. Therefore, in processing high-temporal and high-spatial resolution images, one of the major challenges is to reliably, efficiently and accurately isolate a target/region of interest in large number of images.

High-throughput remote phenotype screening requires integration of aerial platforms with sensors to achieve high spatial, temporal and spectral resolution. Additionally, specific field references are required to precisely process the data and images acquired by the sensor system, resulting in the generation of reliable and accurate data for decision making The present disclosure describes an integrated system for remote sensing including an aerial platform, a sensor system, and an image processing system.

The present disclosure relates to a high-spatial and high-temporal resolution crop sensing system that consists of strategically position ground global positioning system (GPS) reference panels and a GPS guided low-elevation helium balloon based high performance crop sensing platform. High-throughput in-field phenotype screening demands sensors of high spatial, temporal, and spectral resolutions, as well as reliable platforms. Developments in sensors with high-spectral and spatial resolutions offer a unique opportunity in research on in-field high-throughput screening. Yet, traditional platforms, such as fixed-wing aircrafts and/or satellites, are not able to provide data of high enough resolution either spatially or temporally.

In an exemplary embodiment of the present disclosure, a system for monitoring a field of plants includes a plurality of ground based reference objects, each located at a known reference elevation, a known reference latitude, and a known reference longitude, and a balloon adapted to be positioned above the field of plants. The system further includes a balloon positioning system coupled to the balloon and configured to position the balloon relative to the field of plants. An imaging system is supported by the balloon and includes a location system which determines a balloon elevation, a balloon latitude, and a balloon longitude. The imaging system further includes at least one camera, and at least one gimbal configured to orient the at least one camera. The imaging system captures at least one image of the field of plants including the plurality of ground based reference objects in the at least one image.

In another exemplary embodiment of the present disclosure, a method of monitoring a field of plants is provided. The method illustratively includes the steps of positioning a plurality of ground based reference objects relative to the field of plants, each reference object being located at a known reference position including a known reference elevation, a known reference latitude, and a known reference longitude, and obtaining a first aerial image of the field of plants. The first aerial image is taken at a respective image position which corresponds to an image elevation, an image latitude, and an image longitude. The method illustratively further includes the step of assigning a position to each pixel in the first aerial image based on the image position and the known positions of the ground based reference objects captured in the first aerial image.

In a further exemplary embodiment, an aerial positioning system includes a balloon, a balloon positioning system coupled to the balloon and configured to position the balloon at a desired balloon elevation, a desired balloon latitude, and a desired balloon longitude. The balloon positioning system illustratively includes a plurality of winches supported on the ground, and a plurality of tethers extending between the winches and the balloon. A sensor system is supported by the balloon and includes a location system which determines a balloon elevation, a balloon latitude, and a balloon longitude. The sensor system further includes at least one sensor directed to a ground based region of interest, and at least one gimbal configured to orient the at least one sensor. A controller is in communication with the balloon positioning system and the sensor system, wherein the at least one sensor provides to the controller a first set of data related to the region of interest at a first time and a second set of data related to the region of interest at second time. The balloon positioning system positions the balloon at the desired balloon elevation, the desired balloon latitude, and the desired balloon longitude at both the first time and the second time in response to input from the location system.

In another exemplary embodiment, an aerial sensing system includes a plurality of ground based reference objects, each located at a known reference elevation, a known reference latitude, and a known reference longitude. The plurality of ground based reference objects each include a position reference panel having a unique identifier. An aerial platform is adapted to be position above a focus area including objects of interest. An aerial platform positioning system is coupled to the aerial platform and is configured to position the aerial platform at a desired aerial platform elevation, a desired aerial platform latitude, and a desired aerial platform longitude. An imaging system is supported by the aerial platform and includes a location system which determines an aerial platform elevation, an aerial platform latitude, and an aerial platform longitude. At least one camera obtains an aerial image of the objects of interest, the unique identifier being visible to the imaging system to identify the position reference panels. At least one gimbal is configured to orient the at least one camera. A position sensor is operably coupled to the gimbal for detecting the orientation of the at least one camera. The imaging system captures at least one image of the focus area including the plurality of objects of interest and the plurality of ground based reference objects in the at least one image. A controller is in communication with the aerial platform positioning system and the imaging system, the controller including a driving computer that controls the aerial platform positioning system in response to input from the location system, and an imaging computer that processes data from the at least one camera.

The above mentioned and other features of the invention, and the manner of attaining them, will become more apparent and the invention itself will be better understood by reference to the following description of embodiments of the invention taken in conjunction with the accompanying drawings.

BRIEF DESCRIPTION OF THE DRAWINGS

The detailed description of the drawings particularly refers to the accompanying figures in which.

DETAILED DESCRIPTION OF THE DRAWINGS

Figure 1:
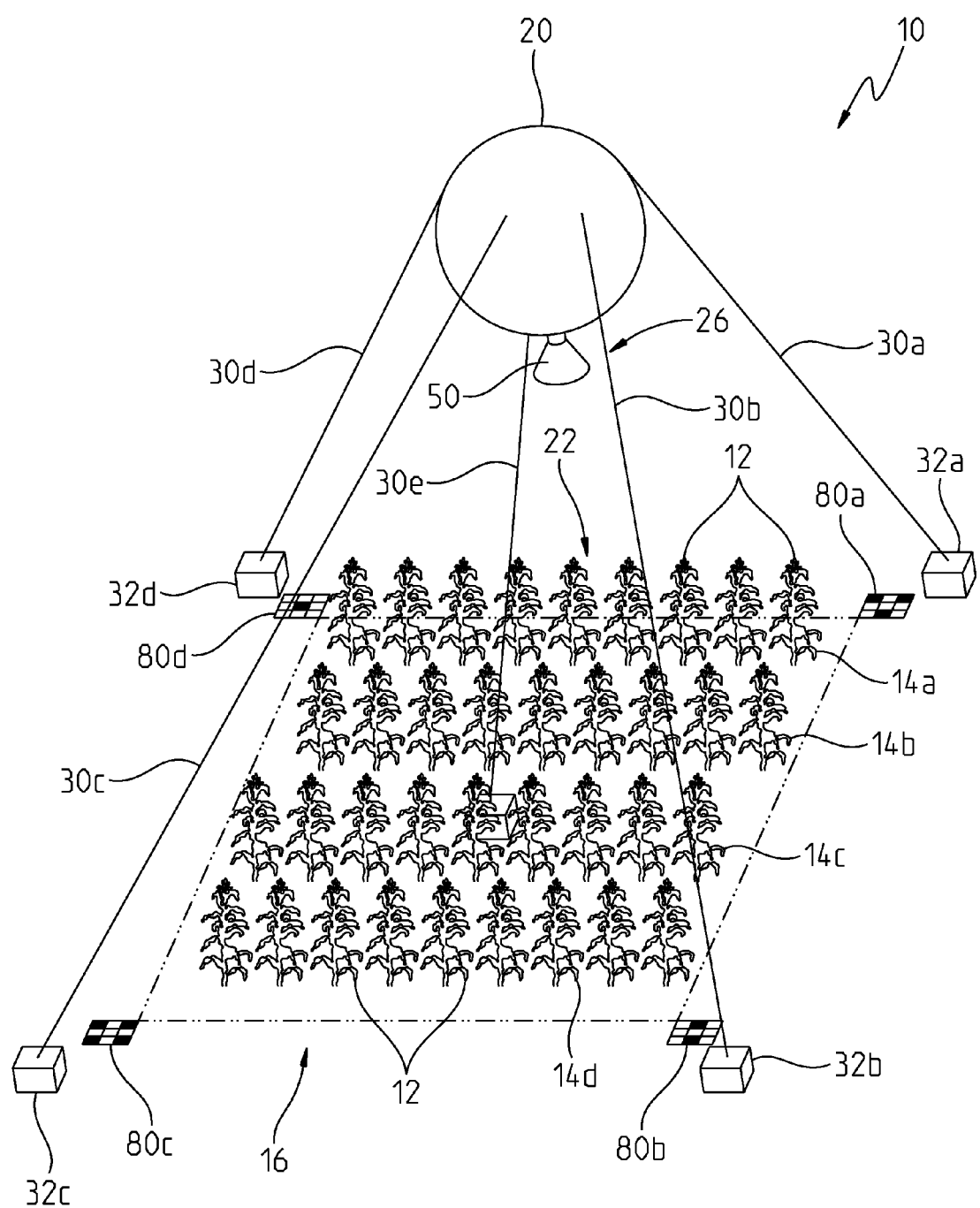
FIG. 1 is a perspective view of an illustrative crop monitoring system of the present disclosure.

The embodiments disclosed below are not intended to be exhaustive or to limit the invention to the precise forms disclosed in the following detailed description. Rather, the embodiments are chosen and described so that others skilled in the art may utilize their teachings. While the present disclosure is primarily directed to monitoring crops, it should be understood that the features disclosed herein may have other applications.

Referring initially to FIGS. 1-4, a monitoring system 10 is configured to monitor a plurality of objects of interest, illustratively plants 12 arranged in a plurality of spaced apart rows 14a, 14b, 14c, 14d in a field 16. The monitoring system 10 includes an aerial platform, illustratively a balloon 20 filled with a lighter than air gas, such as helium, that floats above the ground 22. An aerial platform or balloon positioning system 24 is coupled to the balloon 20 and is configured to position the balloon 20 relative to the field 16 of plants 12. A sensor system 26 is supported by the balloon 20 and is configured to capture data from the field 16 of plants 12. The helium filled balloon 20 provides buoyancy that raises the sensor system 26 into the air for an extended period of time.

The ground based aerial platform or balloon positioning system 24 positions and stabilizes the balloon 20 and the sensor system 26, and also moves the balloon 20 and sensor system 26 anywhere in a defined three-dimensional space above the field 16. More particularly, the balloon positioning system 24 controls the elevation, latitude and longitude of the balloon 20. The balloon positioning system 24 illustratively includes a plurality of tethers or cables 30a, 30b, 30c, 30d, 30e and winches 32a, 32b, 32c, 32d, 32e. The winches 32 are supported by the ground 22 and are coupled to the cables 30. More particularly, the cables 30 are each drawn onto a drum or reel (not shown) of the respective winch 32 to retract or release the cables 30.

First and second cables 30a and 30b cooperate with winches 32a and 32b, and third and fourth cables 30c and 30d cooperate with winches 32c and 32d to control the lateral position (x-axis 34 in FIG. 2) and the longitudinal position (y-axis 36 in FIG. 2) of the balloon 20. Fifth cable 30e cooperates with winch 32e to control the elevation of the balloon 20 (z-axis 38 in FIG. 2).

Figure 2:
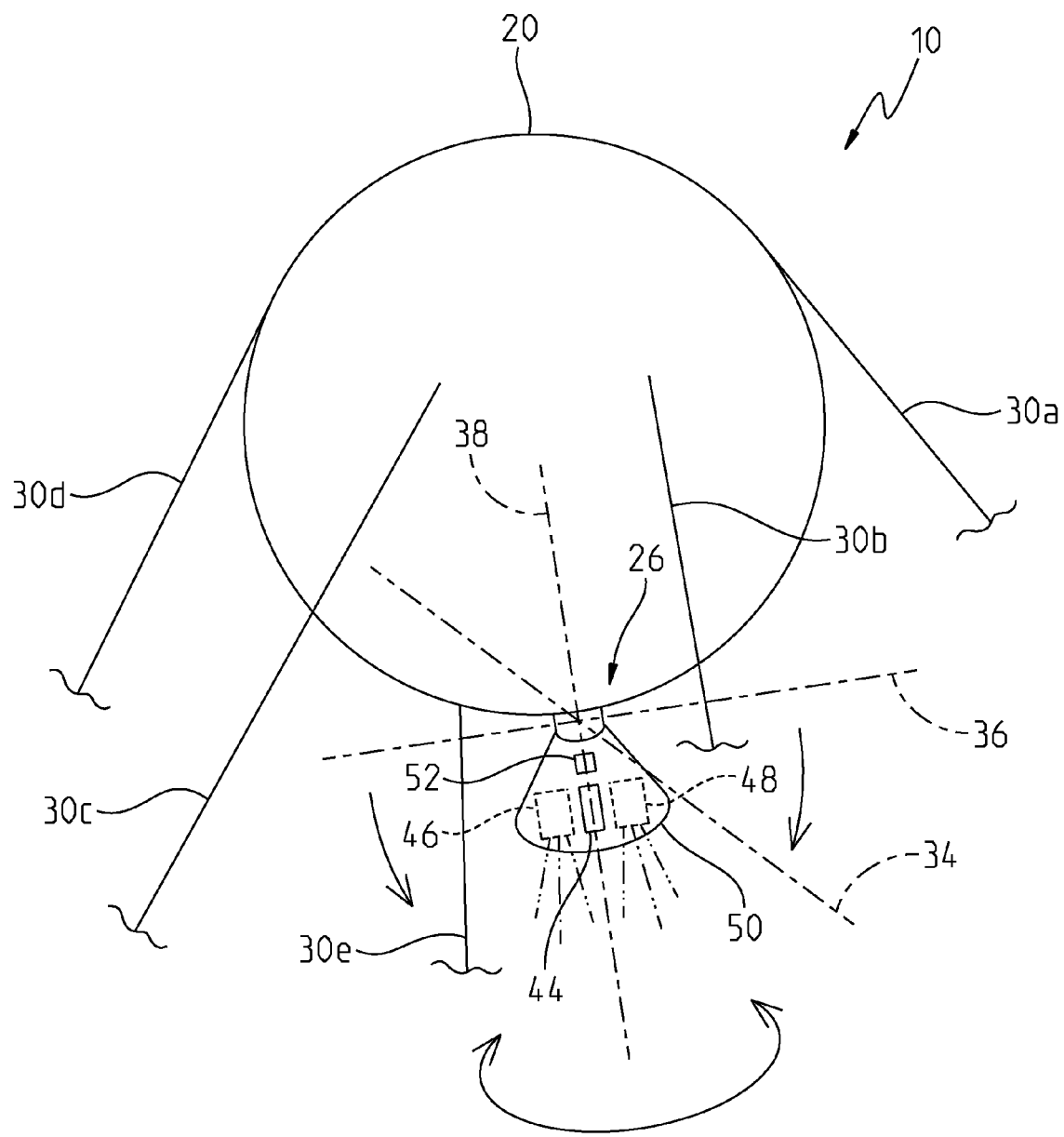
FIG. 2 is a perspective view of an illustrative aerial platform of the crop monitoring system of FIG. 1.
Figure 5:
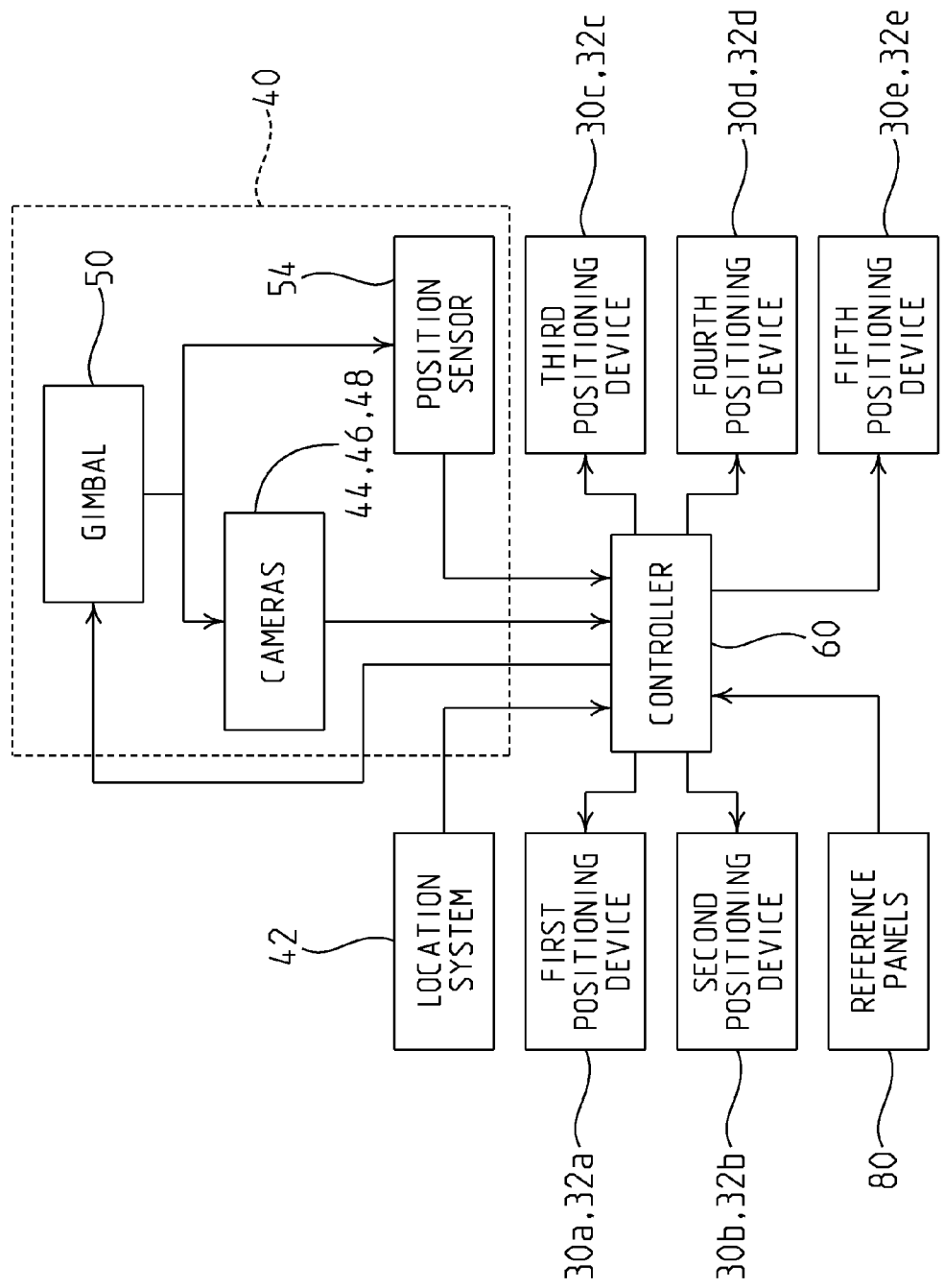
FIG. 5 is a block diagram of functional components of the illustrative crop monitoring system of FIG. 1.

With reference to FIGS. 2 and 5, the sensor system 26 illustratively comprises an imaging system 40, including a location system 42, a plurality of sensors (illustratively cameras 44, 46, 48), and at least one gimbal 50 configured to orient the cameras 44, 46, 48. The location system 42 illustratively comprises a high-precision digital global positioning system (digital GPS or DGPS) receiver 52 that detects the elevation, latitude and longitude of the balloon 20. With the guidance of the DGPS receiver 52, the balloon 20 is capable of establishing precise locations or travelling along pre-defined tracks above the field 16. In certain embodiments, an altimeter may be used to detect the elevation of the balloon 20. The balloon 20 may be deployed quickly, is flexible and persistent, and is configured to provide aerial sensing at well-defined positions repeatedly in a timely fashion.

The gimbal 50 illustratively comprises a smart gimbal controlled remotely. The gimbal 50 may be driven in rotation about x, y and z axes 34, 36 and 38 by a conventional actuator, such as one or more electric motors (not shown). More particularly, the gimbal 50 is configured to rotate approximately 180 degrees about the x and y axes 34 and 36, and rotate approximately 360 degrees about the z axis 38. The cameras 44, 46, 48 are coupled to the gimbal 50, wherein the gimbal 50 points the cameras 44, 46, 48 at the appropriate viewing angles to acquire images in the field 16. At least one position sensor 54 is operably coupled to the gimbal 50 and detects the angular orientation of the gimbal 50 (and therefore the targeting orientation of cameras 44, 46 and 48) about the x, y and z axes 34, 36 and 38. In other words, the position sensor 54 detects the viewing angles of the cameras 34, 36 and 38.

With the data from the DGPS receiver 52, the location system 42 may record the balloon 20 position (balloon longitude, balloon latitude and balloon elevation), while the balloon positioning system 24 may reposition the balloon-based sensor system 26 into precisely the same position and trajectory in observations made in different days and times. The position sensor 54 on the smart gimbal 50 provides the capability to orient the gimbal 50 and thereby point the cameras 44, 46, 48 to the target (e.g., field 16) using the same viewing angle every time an image is taken. With this setup, the relative geometrical relationship between the cameras 44, 46, 48 and the target will be maintained in all images taken at different times, therefore the relative positions of the targets of interests will be maintained in all images taken at difference times.

Camera 44 illustratively comprises a multispectral camera supported by the gimbal 50 and configured to acquire at least one image in a plurality of channels of the electromagnetic spectrum. As is known, a multispectral image captures image data at specific frequencies across the electromagnetic (EM) spectrum. In the illustrative embodiment, the multispectral camera 44 is configured to acquire images in five different channels: red, green, blue, near-infrared 1 (NIR 1) and near-infrared 2 (NIR 2). Illustratively, the multispectral camera is an MS-4100 camera available from Optech of Rochester, N.Y.

Camera 46 illustratively comprises a thermal imaging camera supported by the gimbal 50 in parallel to the multispectral camera 44. By cameras 44 and 46 being positioned in parallel, it is ensured that the cameras 44 and 46 are both aimed at the same target when capturing images. The thermal imaging camera 46 is configured to receive at least one image in a desired thermal wavelength. Illustratively, the thermal imaging camera 46 acquires images in a mid-range thermal wavelength (i.e., 8-13 micron). In one illustrative embodiment, camera 46 comprises an FLIR SC-645 camera available from FLIR Systems of Boston, Massachusetts.

Camera 48 illustratively comprises a digital camera fixed to the side of camera 44 and positioned in parallel with cameras 44 and 46. The digital camera 48 provides a visual feedback to the operator and therefore a confirmation of the targeting of cameras 44 and 46. The sensor system 26 is flexible such that other camera types may be installed on gimbal 50 as substitutes for, or in addition to, cameras 44, 46, 48.

A ground-based controller 60 is in communication with the balloon positioning system 24 and the sensor system 26. The controller 60 illustratively includes a driving computer 62 that communicates with the balloon positioning system 24, the position sensor 54 and the location system 42, and an imaging computer 64 that processes data from the cameras 44, 46, 48. The driving computer 62 continuously records the balloon position (balloon elevation, balloon latitude and balloon longitude) from the receiver 52, and the x, y and z angles from the position sensor 54 to enable image rectification and/or repositioning to precisely the same position (or trajectory) in subsequent observations (e.g., different times).

Figure 6:
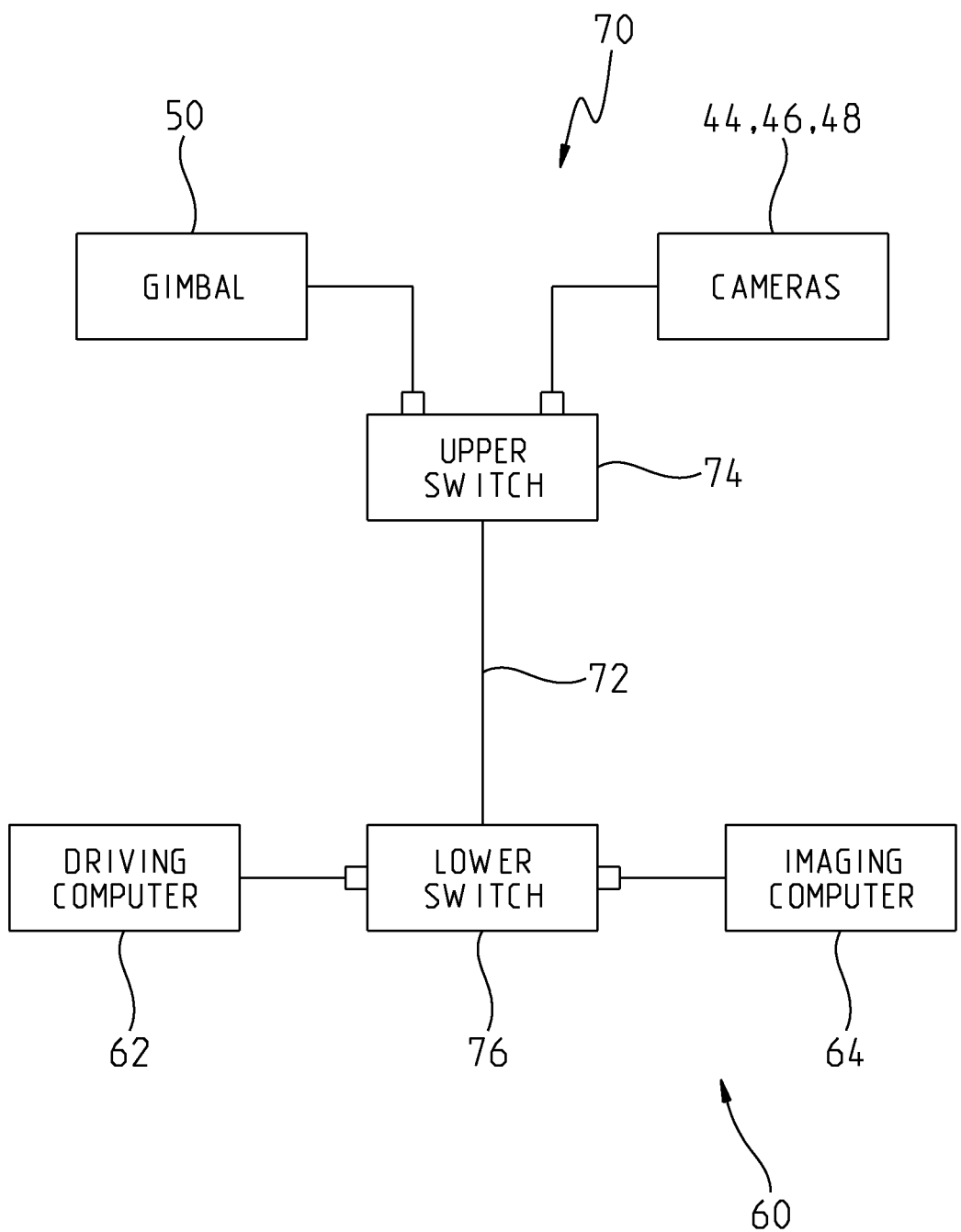
FIG. 6 is a diagrammatic view of the network electrically coupling the aerial platform and the controller.

With reference to FIG. 6, a local network 70 permits the cameras 44, 46, 48 and computers 62, 64 to share a single Ethernet cable 72 for data and command transferring. The local network 70 includes an upper internet switch 74 and a lower internet switch 76 coupled to opposing ends of the cable 72. The upper internet switch 74 is carried by the balloon 20 and includes ports connected to cameras 44, 46, 48 and cable 72. The lower internet switch 76 is supported on the ground 22 and includes ports connected to the computers 62, 64 and cable 72.

Figure 3:
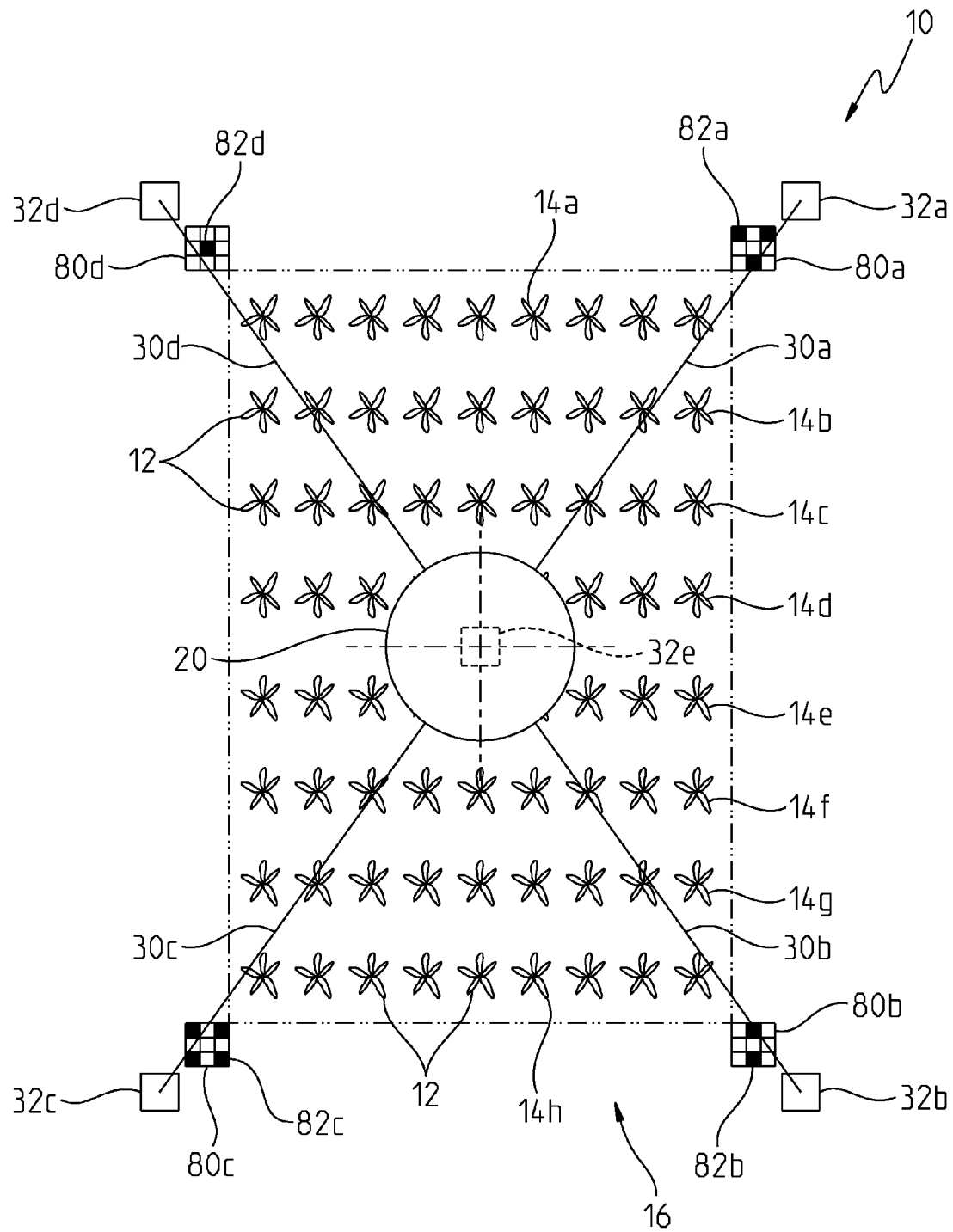
FIG. 3 is a top plan view of the illustrative crop monitoring system of FIG. 1.
Figure 4:
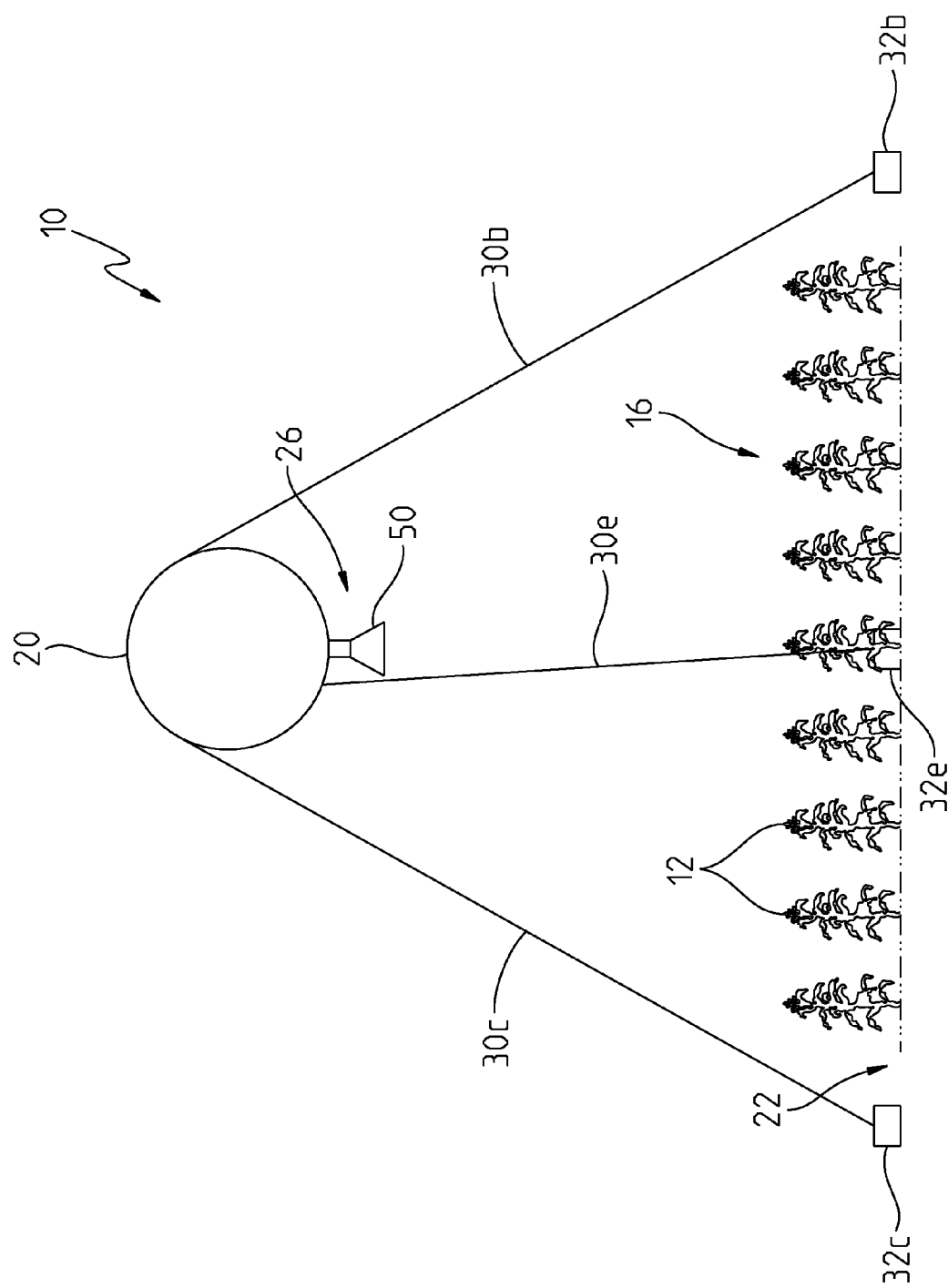
FIG. 4 is a side elevational view of the illustrative crop monitoring system of FIG. 1.

A plurality of ground based reference objects, illustratively reference panels 80a, 80b, 80c, 80d, are positioned in the field 16. High precision GPS data (known reference longitude, known reference latitude and known reference elevation) of these panels 80a, 80b, 80c, 80d are establishing using DGPS systems. The spectral signature of these panels 80 are chosen in a way so that the panels 80 are easily identified and segmented from targets of interest (e.g., plants 12) in thermal and hyper-/multi-spectral images. These reference panels 80 also are used to establish GPS coordinates of representative positions for each row 14 of plants 12. Each panel 80 illustratively includes a unique identifier 82, such as symbols or patterns detectable by the imaging system 40 (FIGS. 1 and 3).

With the established GPS-reference panels 80 and their high precision coordinates established in the images captured by cameras 44, 46, 48, a conventional geographic information system (GIS) may be used to link the high precision GPS coordinates of the reference panels 80 with pixels of the panels 80 in the images received by the imaging computer 64 of the controller 60. With this linkage, the imaging computer 64 may establish high precision GPS coordinates of every pixel in the images. Furthermore, with the known GPS coordinates of the established representative positions in each row 14 of plants 12, the imaging computer 64 may precisely and accurately isolate region of interests from each and every image, making the target segmentation in image processing much easier and more efficient.

As further detailed herein, acquired images go through steps of image pre-processing and data-mining/information extraction. In image pre-processing, radiometric or reflectance calibration and ortho-/geo-rectification are conducted. Radiometric or reflectance calibration removes/reduces differences caused by changes in radiation conditions, and ortho-/geo-rectifications correct/remove distortions caused by relative movements between the targets and the sensors. In the process of geo-rectification, a GIS system within the controller 60 corrects the image distortions by aligning the GPS reference panels 80 in the images to their known GPS coordinates (known as shape-files or maps).

Since the high precision GPS coordinates of the GPS reference panels 80 and each row 14 of plants 12 have been established after conducting geo-rectification, each pixel in the image is "tagged" with its own GPS coordinates. These coordinates establish linkage of the same target in different images acquired in the same time, or images taken at different times.

In data-mining/information extraction, region of interests (ROIs) for each row 14 in every image is established using the established GPS coordinates in the images. Thermal and multispectral vegetative indices, such as crop water stress index, canopy temperature depression. NDVI, VI, etc. is then calculated for each ROI. Snapshot and temporal trends of each ROI is established from the image series to extract both single time point and diurnal trend information.

Figure 7:
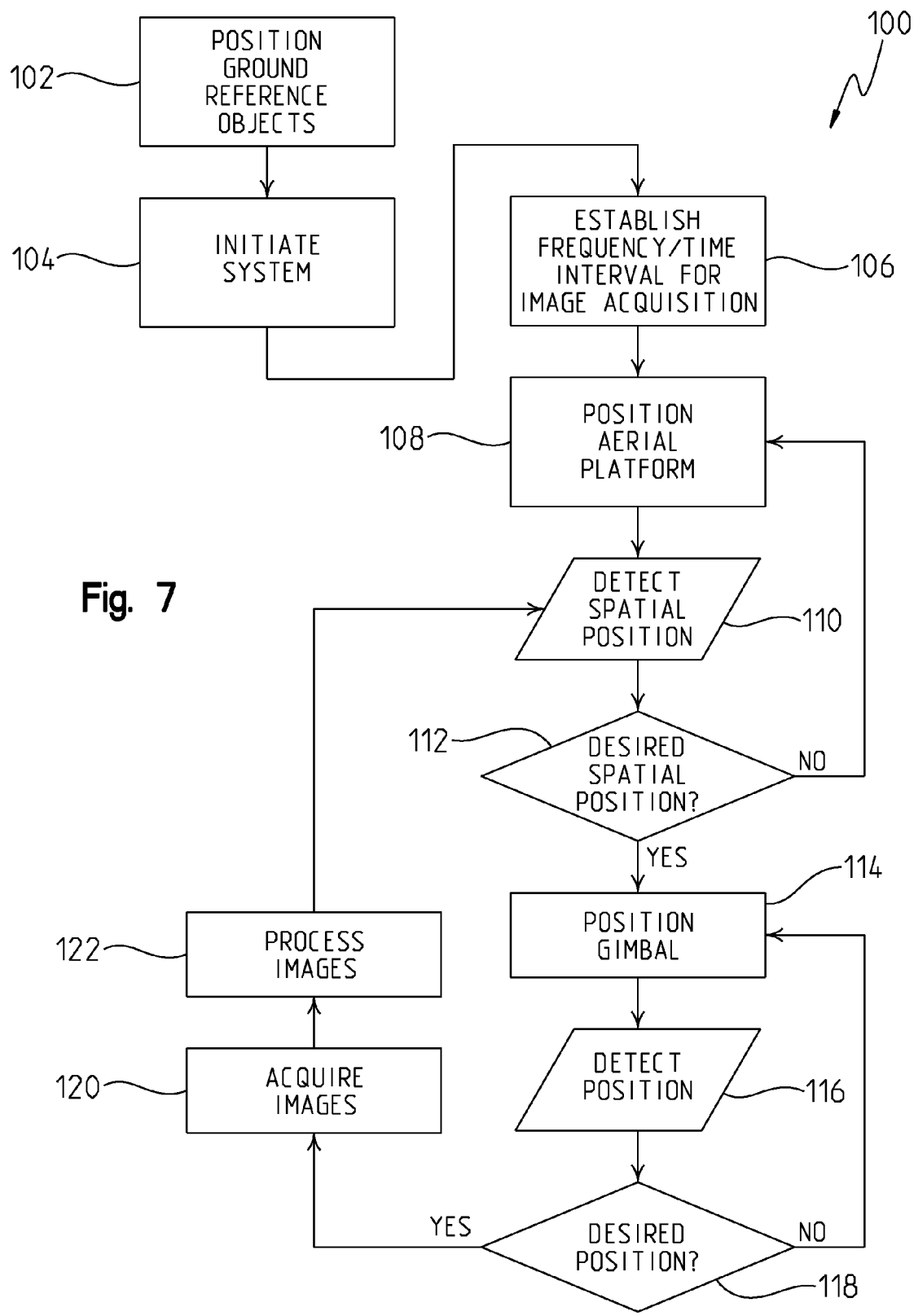
FIG. 7 is a flow chart of an illustrative method of operation of the crop monitoring system of FIG. 1.

With reference to FIG. 7, further details of an illustrative method of operation 100 are shown. At block 102, the ground reference objects or panels 80 are positioned in respective locations in the field 16 of interest, illustratively along the periphery. In one illustrative embodiment, reference panels 80a, 80b, 80c, 80d are positioned in the opposing four corners of a rectangular field 16 of plants 12. As detailed herein, to help in the pre and post processing of images (geo-metric rectification, image registration, etc.), position reference panels 80 are established in each field 16 when images are captured by cameras 44, 46, 48.

At block 104, the monitoring system 10 is initiated. More particularly, power is supplied to the balloon positioning system 24, the sensor system 26 and the controller 60. This includes providing power to the winches 32, and the computers 62 and 64, the location system 42 and the position sensor 54. The driving software of the cameras 44, 46, 48 is also activated. Differential GPS coordinates (illustratively having sub-inch spatial accuracy) of each of the panels 80 are established. Differential GPS coordinates at one end of each single row 14 of each plant 12 are also acquired. These differential GPS coordinates are used in geometric rectification of the images. More particularly, through image registration operations, each pixel (and therefore each row 14 of plants 12) in each image is tagged with GPS coordinates, which helps when linking the images in a GIS system to other environmental data as well as the final yield map.

A standard reflectance panel is established in every multispectral image taken by camera 44. The reflectance panel is used for radiometric calibration of each image.

A cool surface and a hot surface are also established for each thermal image taken by camera 46. In an illustrative embodiment, these surfaces are established by setting up a wet tub and a dry tub at the side of each field 16. Data from these surfaces are used to establish a crop water stress index (CWSI) together with the data acquired from different rows 14 of plants 12.

At block 106, a user inputs into the controller 60 through a conventional interface desired frequency (time interval) for image acquisition by the monitoring system 10. At block 108, the balloon position system 24 positions the balloon 20 at a predetermined spatial position, or predetermined balloon position (balloon elevation, balloon latitude and balloon longitude) which is stored in the controller 60. More particularly, the user ascends the helium-filled balloon 20, and the balloon positioning system 24 controls winches 32 and cables 30 to position the balloon 20 as desired.

At block 110, the location system detects the spatial position of the balloon 20, or detected balloon position. More particularly, the GPS receiver 52 determines the balloon latitude and longitude. In certain embodiments, the GPS receiver 52 also determines the balloon elevation. In other embodiments, an altimeter determines the balloon elevation. If at block 112 the detected balloon position does not equal the predetermined balloon position, then the process returns to block 106 where the balloon positioning system 24 repositions the balloon 20 to the predetermined balloon position. If the detected balloon position equals the predetermined balloon position, then the process proceeds to block 114.

With further reference to FIG. 7, at block 114 the gimbal 50 is positioned at a predetermined angular position of the gimbal 50, or predetermined gimbal position (i.e., x, y and z axes of gimbal 50). At block 116, the position sensor 54 detects the angular position of the gimbal 50 and cameras 44, 46, 48, or detected gimbal position. The digital camera 48 may provide feedback to the controller 60 to ensure that the target field 16 is in the field of view of the camera 48. If at block 118 the detected gimbal position does not equal the predetermined gimbal position, then the process returns to block 114 where the gimbal 50 is repositioned to the predetermined gimbal position. If the detected gimbal position equals the predetermined gimbal position, then the process proceeds to block 120.

At block 120, the image acquisition process begins, where cameras 44 and 46 acquire images of the field 16 of interest. At block 122, the images are processed by the imaging computer 64 of the controller 60. In an illustrative embodiment, the camera 44 provides data/image files to the imaging computer 64. The imaging computer 64 converts the supplied files into .jpg files, illustratively using commercially available software for spectral image processing and geospatial analysis. In an illustrative embodiment, ENVI software available from Exelis Visual Information Solutions of Boulder, Colo. is used by the imaging computer 64. A custom software program may also be used, illustratively one which is compatible with FLIR's ThermoVision SDK, to streamline the process.

The image processing of block 122 includes geo-rectifying the images. In the process of geo-rectification, a GIS system corrects the image distortions by aligning the GPS reference panels in the images to their known GPS coordinates (known as shape-files or maps).

The next step is reflectance or radiometric calibration of the images. Radiometric calibration removes/reduces differences caused by changes in radiation conditions; ortho-/geo-rectifications correct/remove distortions caused by relative movements between the targets (e.g., plants 12) and the sensors (e.g., cameras 44, 46).

Regions of interest (ROI) are then established in each image. Illustratively, ROIs are established for each row 14 in every image using the established GPS coordinates in the images. Since the high precision GPS coordinates of the GPS reference panels 80 and each row 14 of plants 12 have been established after geo-rectification, each pixel in the image is "tagged" with its own GPS coordinates. These coordinates establish linkage of the same target in different images acquired in the same time, or images taken at different times.

The imaging computer 64 of the controller 60 next performs data-mining/information extraction. More particularly, the imaging computer 64 illustratively calculates the value of thermal and multispectral vegetation indices (e.g., crop water stress index, canopy temperature depression, NDVI, VI, etc.) for each ROI. Next, the imaging computer 64 establishes time sequences of surface temperature, as well as vegetation indices for each ROI. The imaging computer 64 may then statistically analyzes data and selects candidates (e.g., plants) for advancement.

The imaging computer 64 of the controller 60 may output the processed data in a variety of formats, including environmental data tables and final yield maps. Following the image processing of block 122, the process returns to block 110 where the location system 42 detects the spatial position of the balloon 20.

The remote sensing system 10 may be used to acquire and process high spatial/temporal resolution data from the ground using any sensor that may be lifted by the aerial platform of the present disclosure. More particularly, by carrying the GPS receiver on the balloon 20, the imaging system 40 is able to be repeatedly placed in the same location at different times. This provides the ability to capture images of the same field of view at different times. The ground based reference panels 80 provide true location objects in the field of view and provide the ability to associate a location coordinate to each pixel in an image. This permits greater efficiency in the identification of objects in the images and image segmentation.

While this invention has been described as relative to exemplary designs, the present invention may be further modified within the spirit and scope of this disclosure. Further, this application is intended to cover such departures from the present disclosure as come within known or customary practice in the art to which this invention pertains.

What is claimed is:
1. An aerial positioning system comprising:
a balloon;
a balloon positioning system coupled to the balloon and configured to position the balloon at a desired balloon elevation, a desired balloon latitude, and a desired balloon longitude, the balloon positioning system including a plurality of winches supported on the ground, and a plurality of tethers extending between the winches and the balloon;
a sensor system supported by the balloon, the sensor system including
a location system which determines a balloon elevation, a balloon latitude, and a balloon longitude,
at least one sensor directed to a ground based region of interest, and
at least one gimbal configured to orient the at least one sensor; and
a controller in communication with the balloon positioning system and the sensor system, wherein the at least one sensor provides to the controller a first set of data at a first time related to the region of interest, and a second set of data at a second time related to the region of interest, and the balloon positioning system positions the balloon at the desired balloon elevation, the desired balloon latitude, and the desired balloon longitude in response to input from the location system at both the first time and the second time.

2. The aerial positioning system of claim 1, further comprising a plurality of ground based reference objects, each located at a known reference elevation, a known reference latitude, and a known reference longitude, wherein the at least one sensor captures the plurality of ground based reference objects in at least one image.

3. The aerial positioning system of claim 2, wherein the plurality of ground based reference objects each include a position reference panel having a unique identifier, the unique identifier being visible to the at least one sensor to identify the position reference panel.

4. The aerial positioning system of claim 1, wherein the at least one sensor comprises a camera.

5. The aerial positioning system of claim 4, wherein the at least one camera includes a multispectral camera for acquiring at least one image in a plurality of channels of the electromagnetic spectrum.

6. The aerial positioning system of claim 5, wherein the at least one camera further includes a thermal imaging camera supported in parallel to the multispectral camera, the thermal imaging camera configured to receive at least one image in a desired thermal wavelength.

7. The aerial positioning system of claim 6, wherein the at least one camera further includes a digital camera providing a visual feedback for guidance and target aiming.

8. The aerial positioning system of claim 1, wherein the balloon positioning system includes four winches and tethers for lateral and longitudinal positioning of the balloon.

9. The aerial positioning system of claim 8, wherein the balloon positioning system includes a fifth winch and tether for elevational positioning of the balloon.

10. The aerial positioning system of claim 1, wherein the location system includes a global positioning system receiver for detecting at least the balloon latitude and the balloon longitude.

11. The aerial positioning system of claim 10, wherein the location system further includes an altimeter for detecting at least the balloon elevation.

12. The aerial positioning system of claim 1, wherein the at least one gimbal is configured to rotate the at least one sensor about three axes for pointing the at least one sensor in desired directions to acquire data from the region of interest.

13. The aerial positioning system of claim 12, wherein the at least one gimbal is configured to rotate the at least one sensor 360 degrees about a z-axis, at least 180 degrees about an x-axis, and at least 180 degrees about a y-axis.

14. The aerial positioning system of claim 12, wherein the sensor system includes a position sensor operably coupled to the at least one gimbal and configured to detect the angular orientation of the at least one gimbal and the direction of the at least one sensor.

15. An aerial sensing system comprising:
a plurality of ground based reference objects, each located at a known reference elevation, a known reference latitude, and a known reference longitude, wherein the plurality of ground based reference objects each include a position reference panel having a unique identifier;
an aerial platform adapted to be positioned above a focus area including objects of interest;
an aerial platform positioning system coupled to the aerial platform and configured to position the aerial platform at a desired aerial platform elevation, a desired aerial platform latitude, and a desired aerial platform longitude;
an imaging system supported by the aerial platform, the imaging system including
a location system which determines an aerial platform elevation, an aerial platform latitude, and an aerial platform longitude,
at least one camera for obtaining an aerial image of the objects of interest, the unique identifier being visible to the imaging system to identify the position reference panel,
at least one gimbal configured to orient the at least one camera, and
a position sensor operably coupled to the at least one gimbal for detecting the orientation of the at least one camera, wherein the imaging system captures at least one image of the focus area including the plurality of objects of interest and the plurality of ground based reference objects in the at least one image; and
a controller in communication with the aerial platform positioning system and the imaging system, wherein the controller includes a driving computer that controls the aerial platform positioning system in response to input from the location system, and an imaging computer that processes data from the at least one camera.

16. The aerial sensing system of claim 15, wherein the aerial platform includes a helium filled balloon.

17. The aerial sensing system of claim 16, wherein the aerial platform positioning system includes four winches and cables for lateral and longitudinal positioning of the balloon.

18. The aerial sensing system of claim 17, wherein the aerial platform positioning system includes a fifth winch and a cable for elevational positioning of the balloon.

19. The aerial sensing system of claim 15, wherein the location system includes a global positioning system receiver for detecting at least the aerial platform latitude and the aerial platform longitude.

20. The aerial sensing system of claim 18, wherein the location system further includes an altimeter for detecting at least the aerial platform elevation.

21. The aerial sensing system of claim 15, wherein the at least one camera includes a multispectral camera for acquiring at least one image in a plurality of channels of the electromagnetic spectrum.

22. The aerial sensing system of claim 21, wherein the at least one camera further includes a thermal imaging camera supported in parallel to the multispectral camera, the thermal imaging camera configured to receive at least one image in a desired thermal wavelength.

23. The aerial sensing system of claim 22, wherein the at least one camera further includes a digital camera for guidance and target aiming providing a visual feedback for guidance and target aiming.

24. The aerial sensing system of claim 15, wherein the at least one gimbal is configured to rotate the at least one camera about three axes for pointing the at least one camera in desired directions to acquire images in the field of study.

25. The aerial sensing system of claim 24, wherein the at least one gimbal is configured to rotate the at least one camera 360 degrees about a z-axis, at least 180 degrees about an x-axis, and at least 180 degrees about a y-axis.

26. The aerial sensing system of claim 15, wherein the imaging computer is configured to geo-rectify the images.

27. The aerial sensing system of claim 26, wherein the driving computer is configured to cause the aerial platform positioning system to reposition the aerial platform at the desired aerial platform elevation, the desired aerial platform latitude, and the desired aerial platform longitude in response to input from the location system.

* * * * *